United States Patent [19]

Fahy et al.

[11] 4,427,298

[45] Jan. 24, 1984

[54] METHOD AND SYSTEM FOR ACCURATELY PROVIDING FLUID BLENDS

[75] Inventors: Edward J. Fahy, Wilmington, Del.; John C. Steichen, Landenberg, Pa.

[73] Assignee: E. I. Du Pont de Nemours and Company, Wilmington, Del.

[21] Appl. No.: 430,837

[22] Filed: Sep. 30, 1982

[51] Int. Cl.³ .................................................. B01F 15/02
[52] U.S. Cl. ....................................... 366/132; 366/134; 366/142; 366/152; 366/160; 366/179; 366/182; 137/624.18
[58] Field of Search ................ 137/606, 624.18, 624.2; 210/31 C, 96.1, 141, 659; 222/144.5, 145; 73/61.1 C; 366/131, 132, 134, 142, 160, 162, 177, 179, 182, 348

[56] References Cited

U.S. PATENT DOCUMENTS

| | | |
|---|---|---|
| 3,398,689 | 8/1968 | Allington ................................ 137/99 |
| 3,446,057 | 5/1969 | Bakalyar et al. ................. 73/61.1 C |
| 3,608,869 | 9/1971 | Woodle ................................ 366/132 |
| 3,869,067 | 3/1975 | Ashmead et al. ............. 137/624.18 |
| 4,004,884 | 1/1977 | Zdrodowski ................... 137/624.18 |
| 4,018,685 | 4/1977 | Saunders et al. .................... 210/145 |
| 4,128,476 | 12/1978 | Rock .................................... 210/659 |
| 4,162,689 | 7/1979 | Zdrodowski ........................ 137/266 |
| 4,239,623 | 12/1980 | Schrenker ........................ 73/61.1 C |
| 4,279,360 | 7/1981 | Hauser ................................... 222/1 |
| 4,310,420 | 1/1982 | Konishi et al. ...................... 210/659 |
| 4,341,327 | 7/1982 | Zeitz .................................... 222/63 |

Primary Examiner—Robert W. Jenkins
Assistant Examiner—Arthur D. Dahlberg

[57] ABSTRACT

A method and system are described for preventing interaction between the valves and pump in a liquid blending system. The method and system select operating relationships between the valve period and pump period that avoids synchronous operation and thereby improves the blend accuracy.

11 Claims, 5 Drawing Figures

METHOD AND SYSTEM FOR ACCURATELY PROVIDING FLUID BLENDS

BACKGROUND OF THE INVENTION

This invention relates to a method and system for improving the fluid blending performance of a pumping system.

There are a number of applications in which fluids must be blended in a highly precise manner. This is particularly true in the case of liquid chromatography in which high pressure liquid metering pumps typically are used. Several liquids, each from separate reservoirs, are blended together in a mixer. The blend then flows to a pump for passage to a chromatograph separating column. Each liquid before entering the mixer first passes through a filter to remove solid particulates.

Fluid blending or proportioning is accomplished by means of plural valves (usually solenoid operated) positioned between each reservoir and the mixer. The valves operate during a valve cycle, typically between 5 and 7 seconds. Each valve is open a certain fraction of the valve cycle time $T_v$. In the case of four valves A, B, C, D, while the valve for liquid A is open, the valves for the liquids B, C, and D are closed and so on. The fraction of time each valve is open each valve cycle determines the average concentration of that liquid exiting the mixer.

The pump typically consists of two or more positive displacement pump heads, each operating out of phase to maintain a smooth flow profile. If three pump heads are used, each head's piston is 120° out of phase with the two other pistons. For each pump head, the piston displacement is a sinusoidal function of time. The pump period is determined by the pump delivery volume per cycle divided by the volumetric throughput rate. The inlet and outlet of the pump heads are joined at manifolds, which divide the flow at the pump inlet and combine the flow at the pump outlet. The flow into each pump head is pulsatile, i.e., when liquid is drawn into a pump head cavity by retraction of the piston, there is no flow out of the given cavity, and when liquid is forced out of the cavity by the advancing piston, there is no flow into it. This type of operation is obtained by inlet and exit check valves on each pump head to assure that the heads are drawing and delivering fluids at the proper time in the cycle. Under these conditions the three pump heads, for example, produce six flow pulsations into and out of the pump for each pump cycle.

While these positive displacement pumps are quite capable of providing a highly accurate and reproducible flow rate of the pumped fluids, a problem has arisen in that an interaction can occur between the pump cycle and the valve cycle. This interaction results in a very slow, long-term variation in the concentration of the mixed liquids which is too long to be attenuated by the mixer. In the case of liquid chromatography, the blending error of the different liquids should be less than 0.15% and in all cases must be less than 0.5%. Unfortunately, in typical cases, these blending errors far exceed these limits and hence are an undesirable feature of liquid blending systems. This is particularly true when used in those areas such as liquid chromatography in which a high degree of accuracy is required.

SUMMARY OF THE INVENTION

A method is disclosed for accurately controlling the blending of components, derived from plural reservoirs, by cyclically time proportioning the flow from each reservoir to a mixer in order to form a fluid stream and cyclically pumping the fluid stream to a utilization device comprising the steps of adjusting the cyclic period of the pump to provide a desired flow rate, and adjusting the cyclic period of the time proportioned blending to be asynchronous with the pump cyclic period and its larger harmonics. In a preferred embodiment of the invention, the blending period is adjusted to be asynchronous with the pump period as well as its larger harmonics.

In the method a computer is used to store constants defining plural line segments representing noninteracting straight line relationships between pump frequency (or period) and valve period and to calculate the valve period for a selected pump period by adding the base point of a valve period segment to the product of the slope of that segment's relationship times the difference between the base point of pump frequency for that valve period segment and the selected pump frequency. The exact values of the constants are abitrary, but they must not produce line segments containing points which can be described by the interactive relation $$T_v = \frac{nk}{lmf_p}$$

where $f_p$ is the pump frequency or inverse of the pump period, $T_p$, l is the number of pump heads in the pump, n and m are low valued integers, $T_v$ is the valve period, and k is a conversion factor.

A fluid blending system is also described. The system is designed to accurately control the composition of a blend of fluids from a plurality of reservoirs and includes a mixing chamber, a plurality of valves for selectively permitting the passage of fluids from the reservoirs to the mixing chamber, a pulsatile pump, having a pump period $T_p$, for passing fluid from the mixing chamber, and a controller for selectively providing a valve signal to open and close the valves during a period $T_v$, thereby to vary the composition of the fluid blend, and a pump drive signal to control the pump rate. The system is improved in accordance with this invention by use of a computer in the controller that is responsive to the pump drive signal for adjusting the period of the valve signal to be asynchronous with the pump rate and its harmonics, whereby the fluid blend is maintained at its desired value.

In a preferred embodiment, the computer means stores constants defining plural straight line segments representing the noninteractive relationship between the pump frequency and valve period, and calculates the valve period for a selected pump frequency by adding the base point of a valve period segment to the product of the slope of that segmental relationship times the difference between the base point of pump frequency for that valve period segment and the selected pump frequency in order to ascertain the desired valve period.

In one alternative to the method of this invention, when only two fluids are blended, the ratio of the pump period to the valve period can be selected so that the fluid flow harmonics coincide with the missing harmonics in the flowrate of the fluid flowing from the reservoir.

BRIEF DESCRIPTION OF THE DRAWINGS

The detailed operation of the method and system described briefly above can best be understood by reference to the following figures in which.

DETAILED DESCRIPTION OF THE PREFERRED EMBODIMENT

Figure 1:
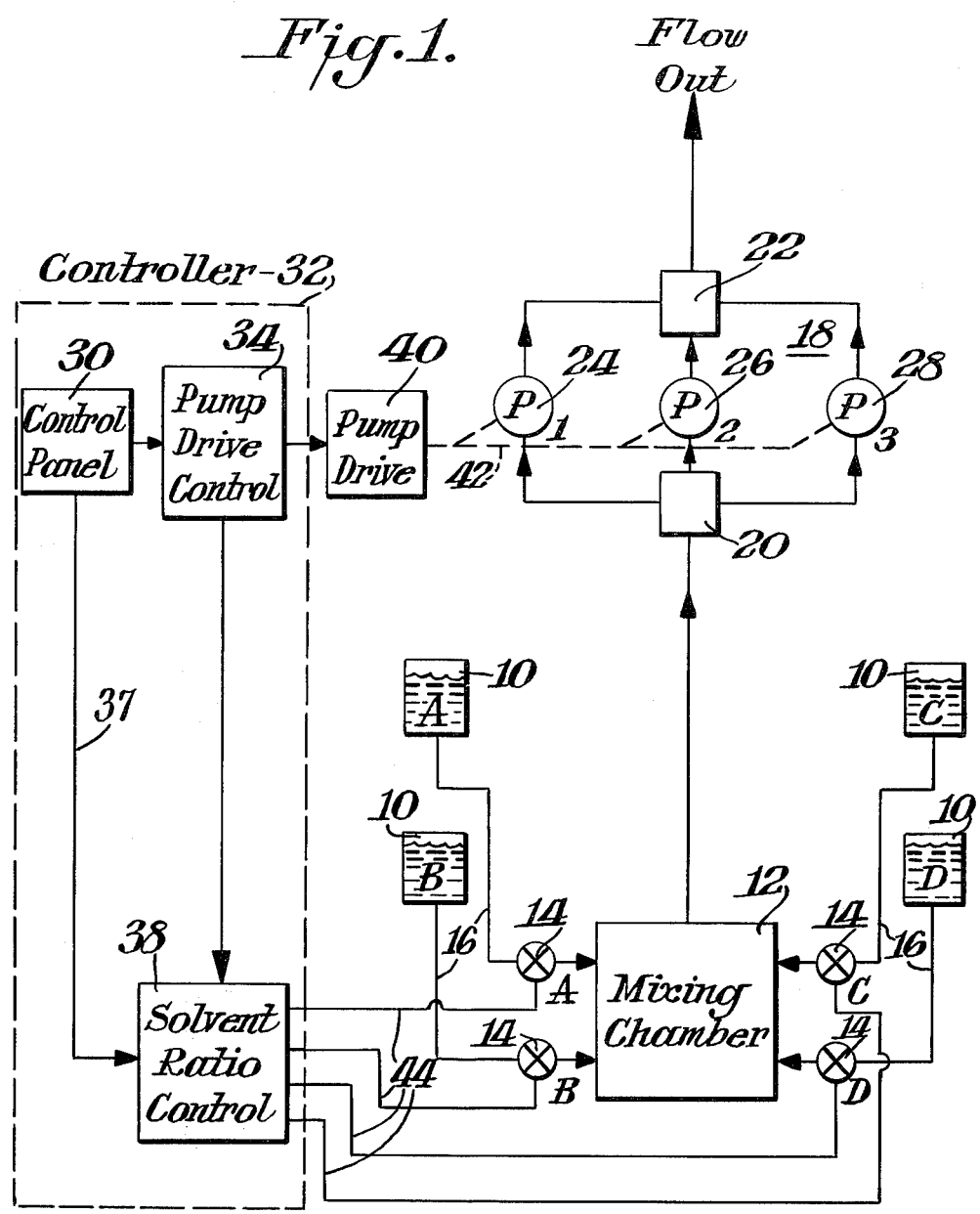
FIG. 1 is a block diagram of a liquid blending system constructed in accordance with this invention.

Although this invention has application with any fluid blending system, it will be described with reference to a particular blending system that finds use in liquid chromatography in which highly precise blends and flow rates must be maintained. Such a system is depicted in FIG. 1. In this system, there is shown a number of reservoirs 10, each holding a different mixable liquid or fluid A, B, C, D. These liquids are to be blended or mixed together in prescribed proportions. To this end, these fluids are each directed to a mixing chamber 12 through conduits 16 and respective solenoid valves 14 denoted A, B, C, D, corresponding to each of the fluid reservoirs 10. Before passing to the mixing chamber, each fluid A, B, C, D is passed through a filter (not shown) which removes solid particulates. Each of the solenoid valves 14 uses a fast acting solenoid which either permits or bars flow along its respective conduit 16.

A blend is formed by periodically opening each valve 14 for a period of time during the total valve period proportional to the fraction of that liquid desired. For example, if a 75% blend of fluid A and 25% blend of fluid B were desired, the A valve 14 would be open for 4.5 seconds and then the B valve 14 open for 1.5 seconds for a total valve period of $T_v$ of 6 seconds. This cycle is repeated each valve period $T_v$. Only one valve is open at a given time. Typically a 5–7 second valve cycle $T_v$ is used in liquid chromatography although other periods can be used as desired.

From the mixing chamber 12, which is conventional as are the solenoids 14, the blended fluid is passed to a pump 18 which includes an inlet manifold 20, an outlet manifold 22 and three pump heads 24, 26 and 28. It is to be understood of course that a pump with one, two or any other number of heads may be used as desired. Typically, however, a three-headed pump is preferred since it provides a more constant level output flow rate. This pump preferably is a positive displacement pump and operated with the heads 120° out of phase. Since this pump is conventional and available commercially it need not be described further. For each pump, the piston displacement is a sinusoidal function of time. The pump period is determined by the pump delivery volume for one cycle of each pump head divided by the volumetric throughput rate of the system.

Figure 2:
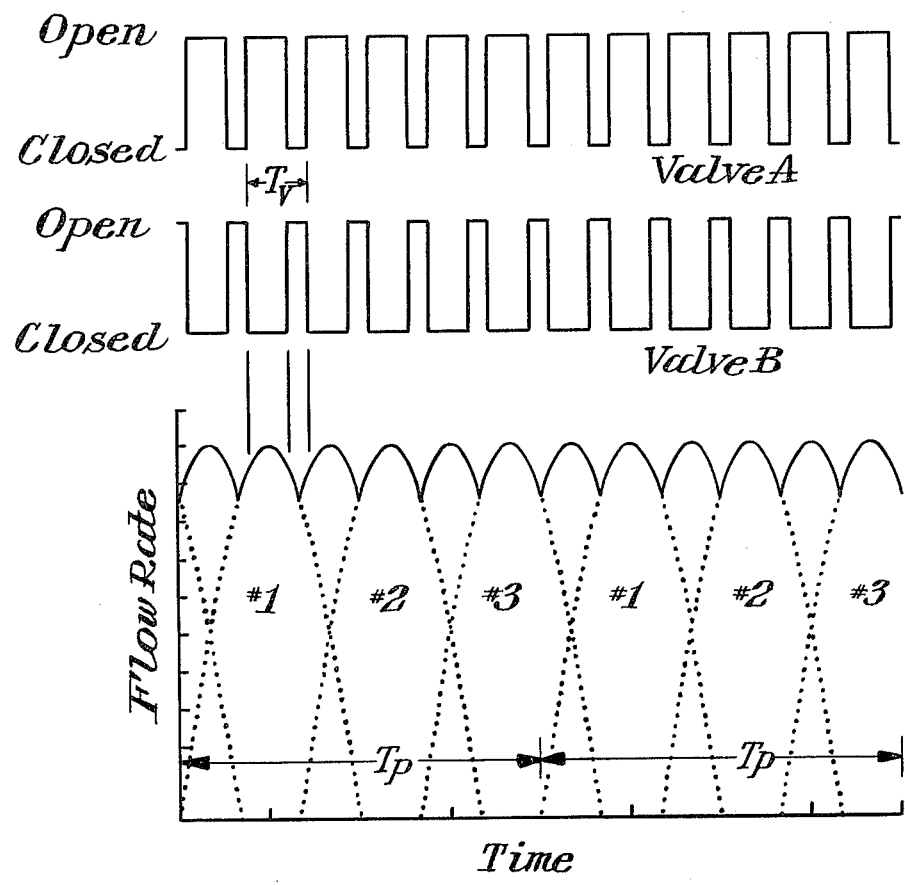
FIG. 2 is a drawing illustrating several of the flow wave forms resulting from fluid flows in the system of FIG. 1 together with valve periods.

Inlet and exit check valves on each pump head (not shown) insure that each head delivers fluid at the proper times in the pump cycle. Thus it may be seen that the inlet and outlet of the pump heads 24, 26 and 28 are joined by the manifolds 20 and 22 which divide the flow at the pump inlet and combine the flow at the outlet. Because of the check valves, the flow into the fluid cavity of each pump head 24, 26 and 28 is pulsatile, i.e., when liquid is drawn into the cavity by retraction of the piston there is no flow out of the given cavity, and when the liquid is forced out of the cavity by the advancing piston, there is no flow into it. The precise characteristics of the flow pulsations depend upon the driving mechanism of the pistons, on the fluid compressibility, and on the check valve response time. Therefore, the three pistons produce six flow pulsations into and out of the pump for each pump cycle an example of which may be seen in the pump flow illustration of FIG. 2.

The controller 32 includes a pump drive control 34 which actuates a pump drive 40, and which in turn drives through the linkages 42 the respective pump heads 24, 26 and 28. The pump drive control 34 operates in response to the desired flow rate information 36 which in turn is set typically by the operator of the system on the control panel 30. The operator also sets the blend composition information 37 which is transferred to a solvent ratio controller 38 by the control panel 30. The open and closed time of each valve is determined by the controller 38 and implemented by energizing the several solenoids 14 at their proper times through control lines 44. Thus far the system described is conventional and may, for example, be that sold by E. I. du Pont de Nemours and Company, Wilmington, DE as their Model 850 HPLC system.

In accordance with this invention, the problem resulting from the periodicity of the pump flow interacting with the periodicity of the solenoid valves to produce slow unexpected variations in the fluid blends is solved. The solution includes modification of the valve period $T_v$ based upon motor rate information obtained by the solvent ratio control 38 from the pump drive control 34. An example of this undesirable interaction may be seen in FIG. 2 where the valves A and B are illustrated as being cycled open and closed over the period $T_v$ during the pump flow period $T_p$. Under these conditions, the valves provide a 67% A 33% B blend. The pulsations of the pump and valves are illustrated as being in perfect synchronization such that maximum flow rate occurs when the valve A is open. Conversely, the minimum flow occurs when the valve B is open since the pump flow was at a minimum during the opening of the valve B. As a result, the blend contains more of component A than expected from the valve period. In actual practice the exact synchronization between the pump period and valve period seldom occurs. Rather there is a slow fluctuation in concentration as the valves and flow pulsations move in and out of phase.

According to the method of this invention, errors in such blending are reduced or eliminated by selecting valve periods which do not cause interaction between the respective valve periods and flow periods. Preferably errors are avoided by setting the valve period to be a function of the flow rate. More specifically the cyclic rate, i.e., period, of the pump is adjusted to provide a desired flow rate and then the time proportioning cyclic rate, i.e., period, of the valves is adjusted to be asynchronous with the pump cyclic rate and the larger pump rate harmonics. In this manner the makeup of the components and the fluid stream is accurately and consistently maintained.

Figure 3A:
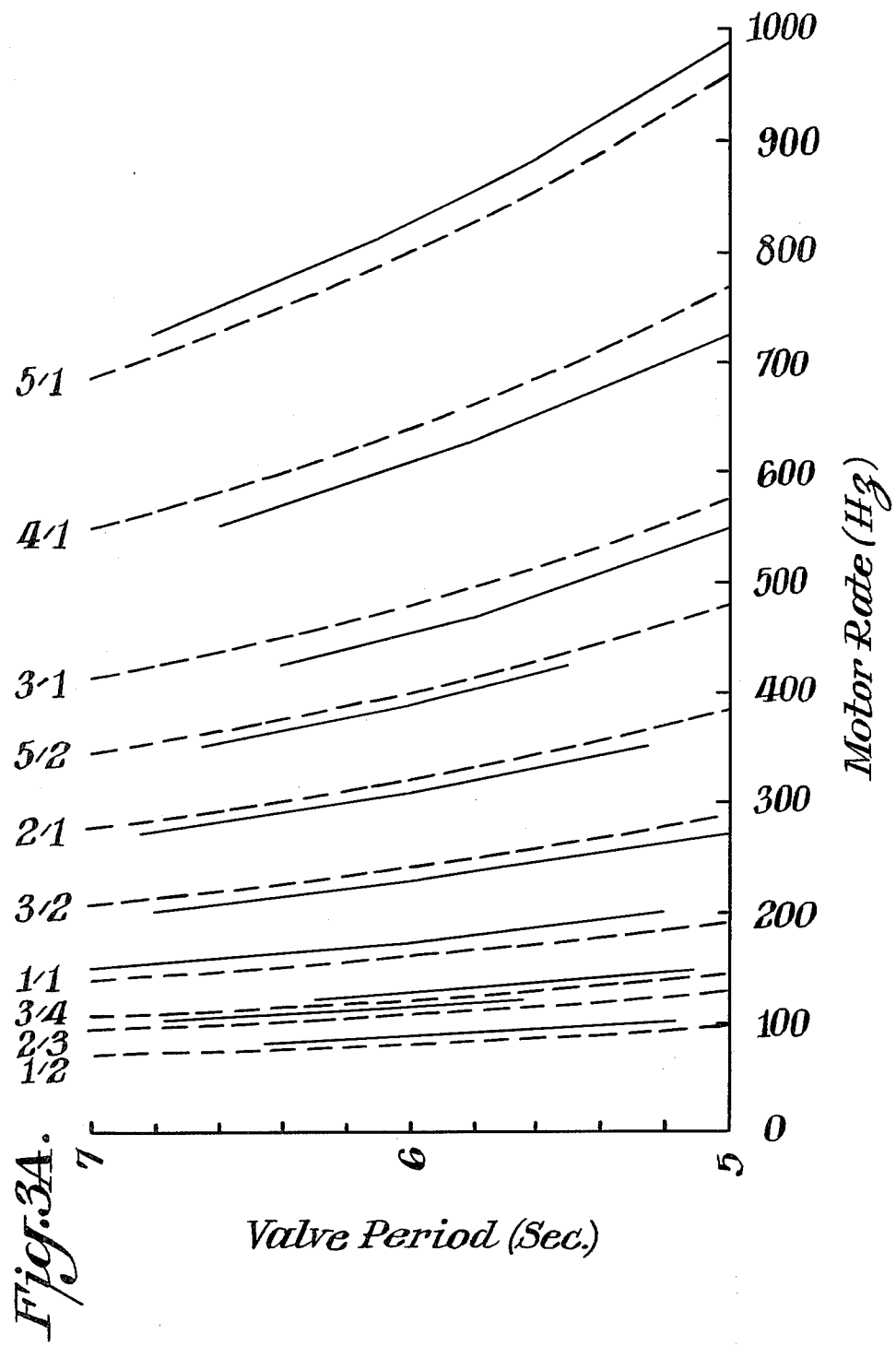
FIGS. 3a and 3b are drawings of the synchronization lines between valve period and motor rate depicting arbitrarily selected line segments which will permit the system of FIG. 1 to avoid deleterious interaction between the pump and valves.
Figure 3B:
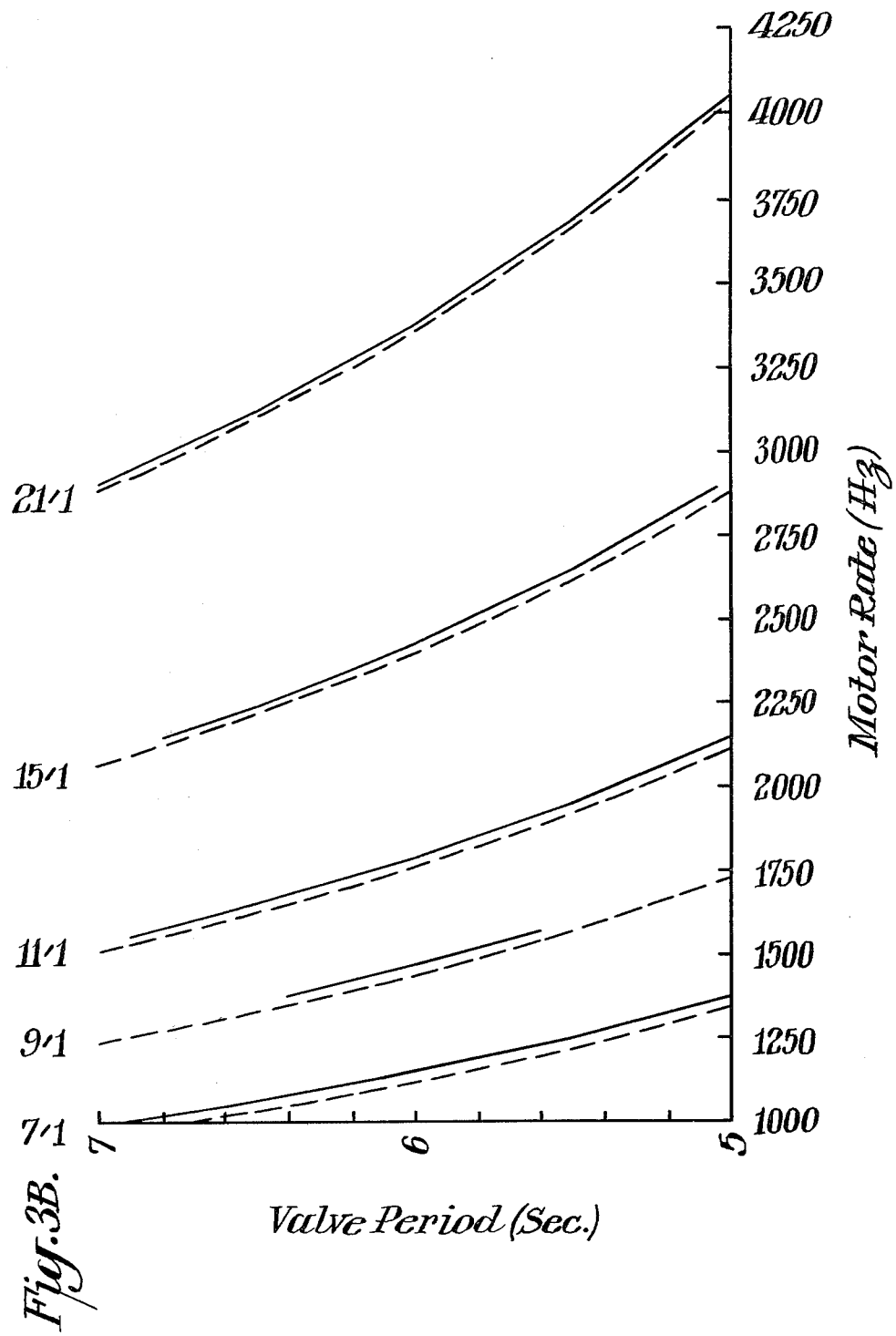

There may be seen in FIGS. 3A and 3B a graphical representation of the resonance relationships between the valve period and the pump or motor rate and for selected major harmonics between the valve period and the motor rate. These relationships are those at which the undesired interactions occur between the pump rate and valve period for a particular pump. Thus the dashed lines 60 bearing the desigations ½, ⅔, ¾, 1/1, etc. represent the regions at which the valve period and the motor rate will interact to cause slowly varying concentrations.

In accordance with this invention, valve periods are selected which do not lie near these interaction or resonance lines. More specifically, blend concentration errors are avoided by deliberately setting the valve period as specified functions of the flow rate, i.e., the motor rate. These specified functions or nonresonant regions are denoted by straight line segments 62 (solid lines) drawn in the graph of FIGS. 3A and 3B. The straight line segments denote safe operating regions for the valve period as a function of motor rate for every motor rate that would typically be used in a particular pumping system. It is noted that as motor rates increase, different harmonics of the valve period and motor rate interact. It will be appreciated, of course, that the relationship illustrated in FIGS. 3A and 3B are for a specific pump, in this case the pump used in the Du Pont Model 850 HPLC unit. Formulas for determining these relationships are discussed below.

Each line segment 62, representing a safe asynchronous operating region, is defined by the formula $$T_v = VPS(I) + MS(I)*(MRS(I) - f_p)$$

where VPS(I), MS(I), MRS(I) are constants described in Table 1 below, depending on the motor rate segment I, and $f_p$ is the desired motor rate. These motor rate segments ranging from 80 Hz to 4050 Hz are shown tabulated in the following table.

TABLE 1

| MOTOR RATE - VALVE PERIOD DEPENDENCE | | | |
|---|---|---|---|
| Segment (I) | Motor Rate (MRS) | Valve Period (VPS) | Slope (MS) |
| 0 | 80 | 6.46 | .0645 |
| 1 | 100 | 6.77 | .0565 |
| 2 | 120 | 6.3 | .0425 |
| 3 | 148 | 7 | .041667 |
| 4 | 172 | 6 | .02857 |
| 5 | 200 | 6.8 | .02857 |
| 6 | 228 | 6.0 | .02381 |
| 7 | 270 | 6.84 | .02211 |
| 8 | 308 | 6. | .017857 |
| 9 | 350 | 6.65 | .0171053 |
| 10 | 388 | 6.0 | .0135135 |
| 11 | 425 | 6.4 | .0139535 |
| 12 | 468 | 5.8 | .0139535 |
| 13 | 550 | 6.6 | .0102564 |
| 14 | 628 | 5.8 | .0082474 |
| 15 | 750 | 6.8 | .0080460 |
| 16 | 812 | 6.1 | .0068493 |
| 17 | 885 | 5.6 | .0057143 |
| 18 | 970 | 7.0 | .0072727 |
| 19 | 1045 | 6.6 | .0057473 |
| 20 | 1132 | 6.1 | .0050847 |
| 21 | 1250 | 5.5 | .004 |
| 22 | 1375 | 6.4 | .0042105 |
| 23 | 1470 | 6.0 | .004 |
| 24 | 1570 | 6.9 | .005 |
| 25 | 1650 | 6.5 | .0037037 |
| 26 | 1785 | 6.0 | .0030303 |
| 27 | 1950 | 5.5 | .0026316 |
| 28 | 2140 | 6.8 | .0031579 |
| 29 | 2235 | 6.5 | .0026316 |
| 30 | 2425 | 6.0 | .0022727 |
| 31 | 2645 | 5.5 | .0018400 |
| 32 | 2895 | 7.0 | .0022727 |
| 33 | 3115 | 6.5 | .0019231 |
| 34 | 3375 | 6.0 | .0016393 |
| 35 | 3680 | 5.5 | .0013514 |

The base or starting point of these straight line segments is selected so that each line is mutually exclusive and does not overlap any other line. The solvent ratio control 38 stores this table and solves the formula using the stored constants for each selected pump rate (motor rate-MRS.) and controls the valve switching accordingly.

Figure 4:
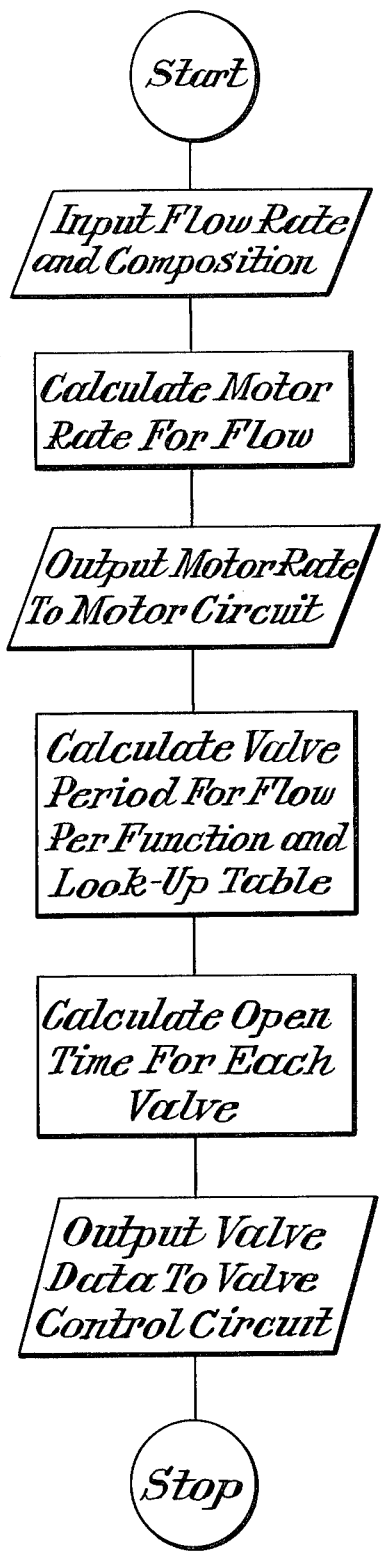
FIG. 4 is a flow diagram showing the manner in which the computation of asynchronous operating valve periods is obtained.

In order to perform this calculation, the solvent ratio control 38 (FIG. 1) has a microprocessor which computes following the flow chart depicted in FIG. 4 in which the flow rate and desired fluid composition are inputs from the operator at the control panel 30. The pump drive control 34 calculates the motor rate needed to achieve such flow and controls the pump drive 40 accordingly for operating the pump heads 24, 26 and 28 at the desired rate. Next, the valve period needed for asychronous or noninteractive operation in accordance with this invention is computed by the solvent ratio control 38. This is accomplished by looking up the necessary constants of stored Table 1 for that desired flow rate $f_p$ to calculate the valve period $T_v$ and from that the open time for each valve. The output valve data is then used during the operating cycle to control the valves 14 to provide the desired blend. At this point the program stops until a new input flow rate and desired blend is inputed into the controller 32 by the operator.

The system of this invention utilizing the controller 32 operates in essentially the same manner as the method just described utilizing the controller with its microprocessor (not shown) which functions with the flow rate and desired blend as inputs to control the pump drive 34 and the solvent ratio control 38.

Alternatively, the controller 32 instead of using a table lookup, may actually compute the valve period from the basic formula. This basic formula may be derived from the following analysis.

CONCENTRATIONS VARIATIONS

If three positive displacement pumps are used in a 120° out-of-phase setup to drive the fluid, then the volumetric flow rate profile Q(t) has a period Tp/3, where Tp is the period of each pump and Q(t) can be represented by $$Q(t) = \overline{Q}\left[1 + \sum_{m=1,2,\ldots} \epsilon_m \sin\left(\frac{6m\pi}{T_p}t + \alpha_m\right)\right] \quad (1)$$

where $\overline{Q}$ is the average flow rate through the system, the constants $\epsilon_m$ are the positive Fourier components of the flow rate and $\alpha_m$ are phase constants.

It can be shown that slowly modulating concentration fluctuations occur of amplitude a given by $$\Delta\alpha \simeq \frac{2}{\pi} \sum_{I} \epsilon \frac{m*I}{n*I} \quad (2)$$

where the sum on I is over positive integers such that $n*I*\alpha$ is not an integer. Here $\alpha$ is the mean concentration of the liquid in question in the pump effluent. The integers n and m are identified by having no common integer factors other than unity and $$\frac{T_p}{3m} = \frac{T_v}{n} \quad (3)$$

where $T_p$ and $T_v$ are the pump and valve cycle periods respectively. The two positive integers n and m thus determine the slow concentration modulation interactions between the pump flow cycle (period $T_p/3$ and the input concentration valve cycle with period $T_v$. Since the period of the concentration modulation $T_v$ can be made large compared with the mean residence time TM in the mixer, it follows that these lines (n,m) in $T_v-T_p$ space must be avoided. High frequency concentration fluctuations are damped by the mixer.

To avoid slowly modulating concentration fluctuations, one must relate a motor rate frequency $f_p$ to the pump piston period $T_p$ by the equation $$f_p = 5760/T_p.$$

The number is a constant which is a function of the motor used, i.e., in this case the Du Pont Model 850. Then the (n,m) resonance or interaction lines, very close to which the concentration of a liquid in the effluent of the LC system slowly modulates, are given by the relation $$f_p = \frac{n}{3m} \frac{5760}{T_v} \quad (4)$$

where n and m have no common integer factors other than unity. Recall (see Eqn. 2) that for a liquid with mean concentration $\alpha$ in the pump effluent, such resonance lines yield slowly modulating concentration fluctuations of amplitude $\alpha$ given by $$\Delta\alpha \simeq \frac{2}{\pi} \Sigma \frac{\epsilon_m}{n} + \ldots \quad (5)$$

where $\epsilon_m$ are the normalized Fourier coefficients of the outlet flow given in Equation (1). Although the magnitude of such concentration fluctuations does depend on $\alpha$, it is neglected in discussing this dependence here. These modulation relationships may be calculated using the above formula and the valve period adjusted to avoid modulation using a computer. Preferably, however, as described previously, to avoid these slow modulation lines for moderate sized integers n and m, a piecewise linear relationship between the motor rate $f_p$ and the valve period $T_v$ of the form $$T_v = VPS(I)*(MRS(I) - f_p) \quad (6)$$

is chosen where VPS(I), MS(I), MRS(I) are constants depending on the motor rate segment I. These motor rate segments ranging from 80 Hz to 4050 Hz are shown tabulated in Table 1. The end points of these straight line segments are calculated from the relationship $$f_p \simeq \left(\frac{n}{m} \pm k_{n,m}\right) \frac{5760}{3*T_v} \quad (7)$$

where m and n have moderate values and thus come close enough to the resonance line (n,m) to avoid crossing other resonance lines with moderate values of (n,m). At the same time the approximating segments are far outside the resonance line width discussed above. The constants $k_{n,m}$ are chosen to ensure the latter. FIGS. 3A and 3B show the calculation graphically with the solid curves denoting different (n,m) resonance curves and the dashed straight line segments the safe $(f_p,T_v)$ relationship of Table 1 and Equation 6. Staying on the solid lines 62 gives a valve period $T_v$ between 5 and 7 secs. appropriate for any motor rate $f_p$ between 80 Hz and 4050 Hz that will avoid slowly modulating concentration variations.

There has thus been described a novel method and system for avoiding slow concentration modulations caused by interacting valve and pump periods.

We claim:

1. A method of accurately controlling the blend of components, derived from plural fluid reservoirs, in a fluid stream by cyclically time proportioning the flow from each reservoir to a mixer to form the fluid stream and cyclically pumping the fluid stream to a utilization device comprising the steps of:
    adjusting the cyclic rate of the pump to provide a desired flow rate, and
    adjusting the time proportioning cyclic rate to be asynchronous with the pump cyclic rate whereby the blend of the components of the fluid stream is accurately maintained.

2. The method of claim 1 wherein the time proportioning rate is adjusted to a value close to but removed from the value representing synchronism between the time proportioning rate and the pump rate.

3. The method of claim 2 wherein synchronism occurs at about $$T_v = \frac{nk}{lmf_p}$$

where $f_p$ is the pump frequency, n and m are integers, l is the number of pump heads in the pump, $T_v$ is the time proportioning period, and k is a conversion factor.

4. The method of claim 1 wherein two fluids are blended and the ratio of the pump period $T_p$ to the time proportioning period $T_v$ is selected so that fluid flow rate Q(t) harmonics coincide with the missing harmonics in the fluid flowing from the reservoirs.

5. The method of claim 1 wherein the time proportioning in cyclic rate is adjusted to be asynchronous with the pump cyclic rate and its larger harmonics.

6. In a fluid blending system for accurately controlling the composition of a fluid blend having a plurality of reservoirs for fluids to be blended, a mixing chamber, a plurality of valves for selectively permitting the passage of fluid from the reservoirs to the mixing chamber, a pulsatile pump having a pump period $T_p$ for passing fluid from the mixing chamber, and a controller for selectively providing a valve signal to open and close the valves during a valve period $T_v$, thereby to vary the composition of the fluid blend, and a pump drive signal to control the pump rate $f_p$, the improvement which includes computer means in the controller responsive to the pump drive signal for adjusting the period of the valve signal to be noninteractive with the pump rate whereby the fluid blend is maintained at its desired valve.

7. The system of claim 6 wherein the computer means adjusts the ratio of the pump period to the valve period so tha harmonics in a two fluid blend flow coincide with the missing harmonics in the fluid flow rate from the reservoirs.

8. The system of claim 7 wherein the computer means determines the valve period at which interaction occurs between the pump and valve periods by the relation $$T_v = \frac{nk}{lmf_p}$$

where f is the pump frequency, 1 is the number of pistons in the pump, n and m are intergers, Tv is the valve period, and k is a conversion factor.

9. The system of claim 7 wherein the computer means stores constants defining plural line segments representing nonresonant relationships between pump frequency and valve period and includes means to calculate the nonresonant valve period for a selected pump frequency by adding the base point of a valve period segment to the product of the slope of that segments relationship times the difference between the base point of pump frequency for that valve period segment and the selected pump frequency.

10. The system of claim 9 wherein the stored constants are the base points of each line segments and the slope of each line segment.

11. The system of claim 6 wherein the computer means is responsive to the pump drive signal to adjust the period of the valve signal to be noninteractive with the pump rate and its harmonics.

* * * * *